United States Patent [19]

Barcomb

[11] Patent Number: 5,759,577
[45] Date of Patent: Jun. 2, 1998

[54] CONTROLLED RELEASE OF STEROIDS FROM SUGAR COATINGS

[75] Inventor: Reginald J. Barcomb, Mooers Forks, N.Y.

[73] Assignee: American Home Products Corporation, Madison, N.J.

[21] Appl. No.: 637,139

[22] Filed: Apr. 24, 1996

Related U.S. Application Data

[63] Continuation-in-part of Ser. No. 373,667, Jan. 17, 1995, Pat. No. 5,547,948.

[51] Int. Cl.$^6$ .......................... A61K 9/36; A61K 31/56; A61K 31/565; A61K 31/57
[52] U.S. Cl. .......................... 424/479; 514/170; 514/171; 514/843; 514/899
[58] Field of Search .......................... 424/479; 514/170, 514/171, 843, 899

[56] References Cited

U.S. PATENT DOCUMENTS

| | | | |
|---|---|---|---|
| 4,154,820 | 5/1979 | Simoons | 424/175 |
| 4,248,856 | 2/1981 | Guley et al. . | |
| 4,309,404 | 1/1982 | DeNeale et al. . | |
| 4,309,405 | 1/1982 | Guley et al. . | |
| 4,390,531 | 6/1983 | Edgren . | |
| 4,425,339 | 1/1984 | Pitchford | 424/239 |
| 4,632,828 | 12/1986 | Carli | 514/178 |
| 4,755,386 | 7/1988 | Hsiao et al. | 424/435 |
| 4,826,831 | 5/1989 | Plunkett et al. | 514/170 |
| 4,927,816 | 5/1990 | Ester | 514/177 |
| 5,073,374 | 12/1991 | McCarty | 424/435 |
| 5,108,995 | 4/1992 | Casper | 514/170 |
| 5,208,225 | 5/1993 | Boissonneault et al. | 514/178 |
| 5,213,808 | 5/1993 | Bar-Shalom et al. | 424/473 |
| 5,223,268 | 6/1993 | Stetsko et al. . | |
| 5,340,589 | 8/1994 | Stetsko et al. . | |
| 5,354,560 | 10/1994 | Lovrecich | 424/489 |
| 5,384,130 | 1/1995 | Kamada . | |
| 5,449,521 | 9/1995 | Lovrecich | 424/489 |
| 5,547,948 | 8/1996 | Barcomb | 514/170 |

OTHER PUBLICATIONS

CA114(18):171312e.
CA113(14):120828z.
CA113(2):12183b.
CA111(24):219315a.
CA110(24):219101g.
CA110(14):121381y.
CA111(20):180687w.
CA106(22):182638b.
Abstract of EP 173928-A.
Abstract of WO8503436-A.
CA103(8):59333j.
CA 103(8):59308e.
Abstract of US 4720387.
CA 102(12):100833s.
CA 100(24):197789b.
CA 100(12):91412h.
Abstract of US 4415546.
Abstract of US 4415547.
Abstract of US 4327076.
Abstract of US 3980766.
CA85(20):149150m.
Abstract of US3437728.
Svensson et al Maturitas 18(3):229–238 Mar. 1994.
Gadan Revista Chilena De Obstetricia y Ginecologia 57(4):283–286 (1992).
FDC reports Pink sheet 15 Apr. 1991 Wyeth-A Yerst[1.] . Premarin sales set sights–premphase—A Phatic estrogen supplement. Premarin IMPA (Prempak) A Combined Estrogen—Progestin Fertility in phase (I) Regimens.
Hargrove et al Obstetrics & Gynecology 73(4):606–612 Apr. 1989.

*Primary Examiner*—Shep K. Rose
*Attorney, Agent, or Firm*—Steven R. Eck

[57] ABSTRACT

A compressed medicinal tablet comprising a tablet core and a sugar coating. said sugar coating containing a dose of a hormonal steroid and a steroid release rate controlling amount of microcrystalline cellulose.

6 Claims, No Drawings

CONTROLLED RELEASE OF STEROIDS FROM SUGAR COATINGS

RELATED APPLICATIONS

This application is a continuation-in-part of co-pending application Ser. No. 08/373,667, filed Jan. 17, 1995, by Reginald J. Barcomb, now U.S. Pat. No. 5,547,948.

BACKGROUND OF THE INVENTION

In the past three decades, substantial effort has gone into the identification of methods for controlling the rate of release of drug from pharmaceutical tablets. Excipients have been incorporated into tablet cores to control dissolution, and hence absorption, of drugs. Tablets and spheroids have been coated with polymers to provide slow, diffusion—controlled release or site-specific release of drugs.

Tablets and encapsulated spheroid dosage forms have also been prepared containing multiple drugs, either in admixture or as separate tablet layers or spheroids. The drugs are provided to perform multiple functions or to provide synergism. Such tablets are especially useful in those circumstances where conventional therapy dictates the use of more than one drug possessing different but compatible activities. For example, diuretic agents are frequently administered with antihypertensive agents, and progestational agents in conjunction with estrogens.

BRIEF DESCRIPTION OF THE INVENTION

In accordance with this invention, there is provided a pharmaceutical tablet comprising an internal compressed core and an external sugar coating, wherein said compressed core optionally contains no pharmacologically-active agent or one or more non-steroidal, pharmacologically-active agents that are conventionally administered in conjunction with a hormonal steroid, the improvement which comprises the incorporation of a hormonal steroid and a hormonal steroid release rate controlling amount of micro-crystalline cellulose in said sugar coating. The compressed tablet core may be devoid of any medicament or it may contain a pharmaceutical agent other than a steroid, that is compatible with the steroid and any other therapeutic agent in the sugar coating. Thus, the sugar coated tablets of this invention may contain one or more pharmacologically-active agents, where the improvement in prior sugar coated tablets comprises the incorporation of a hormonal steroid release rate controlling amount of microcrystalline cellulose in conjunction with a hormonal steroid in said sugar coating. The sugar-coated tablet may be finished with color coatings and polished as is common in coated tablets.

The contents of the tablet core are quite independent from the sugar coating in the sense that the sugar coating and the hormonal steroid contained in it are dissolved before disintegration of the compressed tablet core and dissolution of any drug component present in the core. The excipient components employed in formulation of the core tablet may include pharmaceutically-acceptable water-soluble and/or insoluble substances such as lactose, calcium phosphate, starch, calcium carbonate, dextrose, sorbitol, mannitol, microcrystalline cellulose, sucrose, polyvinylpyrrolidone, methylcellulose, carboxymethylcellulose, alginates, hydroxypropylcellulose, hydroxypropylmethyl-cellulose, ethylcellulose, croscarmellose sodium, sodium starch glycolate, magnesium stearate, stearic acid, polyethylene glycol, sodium lauryl sulfate, fumed silica, talc and the like.

The sugar coat containing the hormonal steroid also contains a steroid release rate-controlling amount of microcrystalline cellulose and, in certain circumstances, polyvinylpyrrolidone to aid in application of the sugar coat.

The tablet core is produced by compression of an admixture, which has preferably been granulated, of the pharmaceutically-acceptable excipients, and, if desired, a therapeutic agent compatible with the steroid to be incorporated with the release rate controlling amount of microcrystalline cellulose in the sugar coating. The tablet core may have an unplasticized or plasticized seal coat designed to modify the drug release characteristics of any drug(s) contained within the core, or to protect them against moisture and/or oxygen. The non-medicated cores are those conventionally employed as placebo tablets in pharmacological studies.

DETAILED DESCRIPTION OF THE INVENTION

This invention provides an improved compressed tablet in which, in addition to a conventional internal tablet core optionally containing no drug or one or more drugs that are pharmacologically compatable with a steroid in the external sugar coating, a sugar coating is present which comprises a hormonal steroid in an amount of about 0.1 to about 20 percent by weight of the sugar coating; microcrystalline cellulose in an amount from about 0.1 to about 3 percent by weight of the sugar coating; polyvinylpyrrolidone in from about 0 to about 5 percent by weight of the sugar coating; and sugar. On a unit dose basis, the tablet contains about 0.01 to about 50 milligrams, preferably about 0.015 to about 40 milligrams and more preferably about 0.02 to 30 milligrams, of total hormonal steroid load in the loaded sugar coating layer. If desired, an undercoat of inert filled sugar may be applied over a seal coat prior to the steroid loaded sugar coat layer. The inert filler-containing sub-layer sugar coating may be made up with sucrose containing about 7.5 to about 15 percent microcrystalline cellulose. The outer sugar coating may contain a coloring agent such as titanium dioxide or a primary, secondary or grayed tint as is customary in the tableting art. If desired, the coloring agent may be applied as a separate coating layer over the outer sugar layer. A final polish may be used to further finish and complete the tablet.

The sugar used in production of the sugar coatings referred to throughout this specification is a sugar product, such as sucrose, derived from beet or cane sources or starch, saccharide or polysaccharide converted sources, which are considered suitable for tablet coating purposes. The currently preferred sugar is sucrose.

It has been discovered that the release of a hormonal steroid from the sugar coating can be controlled by limiting the quantity of microcrystalline cellulose to from about 0.1 to about 3 percent by weight of the sugar coating. This use of a small quantity of microcrystalline cellulose in the sugar coat is unlike the use of this excipient as a compression aid or to assist disintegration of a tablet core. In the latter case, the concentration of microcrystalline cellulose may rise to as high as 15 to 30 percent of weight.

Examples of hormonal steroids suitable for incorporation into the sugar coating formulations of this invention include, for instance, one or more of the following steroids; medroxyprogesterone acetate, levonorgestrel, gestodene, medrogestone, estradiol, estriol, ethinylestradiol, mestranol, estrone, dienestrol, hexestrol, diethylstilbestrol, progesterone, desogestrel, norgestimate, hydroxyprogesterone, norethindrone, norethindone acetate, norgestrel, megestrol acetate, methyltestosterone, ethylestrenol, methandienone, oxandrolone, trimegestone, dionogest, and the like. Additionally, the tissue selective progesterones and/or progesterone antagonists which may or may not have the typical steroidal functionality may be formulated into this technology. These include, but are not limited to: RU-486, onapristone, ZK-137316, ORG-31730, and HRP-2000. Where desired, estrogenic steroids and progestogenic steroids may be used in combination in the sugar coatings.

To illustrate in vitro dissolution rate control of steroid in the absence and presence of microcrystalline cellulose, the following illustrative examples are presented, without limitation:

EXAMPLE 1

A sugar coating consisting of the following solids was applied over a tablet core using either a non-perforated or perforated coating pan:

| Sucrose, NF | 87% |
| Polyvinylpyrrolidone | 3% |
| Medroxyprogesterone Acetate, USP | 10% |

The rate of dissolution of the steroid was determined in accordance with <711> of USP XX, p.959 (1980), employing Apparatus 2, operating at 50 rpm by dissolving in 0.54% sodium lauryl sulfate in water at 37° C. in six repeated trials (Method A). CV represents the coefficient of variation between these trials expressed as a percentage.

| Time (min.) | Percent Steroid Released (CV %) |
|---|---|
| 5 | 93 (5.2) |
| 10 | 94 (5.3) |
| 30 | 95 (5.3) |
| 60 | 95 (5.4) |
| 120 | 95 (5.4) |

EXAMPLE 2

Tablets coated in the same manner with the same sugar coating as above were dissolved in 0.13% sodium lauryl sulfate in 0.1N HCl at 37° C. using USP Apparatus 1 at 100 rpm, in six trials (method B). The results of this study were:

| Time (min.) | Percent Steroid Released (CV %) |
|---|---|
| 5 | 83 (6.0) |
| 10 | 85 (5.8) |
| 30 | 85 (6.2) |
| 60 | 85 (6.1) |
| 120 | 85 (6.2) |

EXAMPLE 3

Additional tablets coated in the same manner with the same sugar composition were subjected to a flow-through dissolution test procedure in 0.12% sodium lauryl sulfate in 0.1N HCl at 37° C. using a SOTAX Dissotest Apparatus at 5.7 mL/min. flow rate (Method C). The results of three separate runs were as follows:

| Time (min.) | Percent Steroid Released (CV %) |
|---|---|
| 30 | 90.9 (2.9) |
| 60 | 94.2 (3.0) |
| 90 | 95.3 (2.9) |
| 120 | 96.0 (3.0) |
| 210 | 97.4 (3.0) |
| 300 | 98.9 (3.6) |

From these in vitro studies it is clear that medroxyprogesterone acetate, used here as a typical steroid, is released from the sugar coating extremely rapidly.

EXAMPLE 4

For comparison purposes, and to illustrate the unexpected properties of the sugar coatings of this invention, a sugar coating consisting of the following solids was applied over a tablet core:

| Sucrose, NF | 86.5% |
| Microcrystalline Cellulose | 0.5% |
| PVP | 3.0% |
| Medroxyprogesterone Acetate, USP | 10.0% |

Employing the microcrystalline cellulose—containing sugar coated tablets and following Method A, the following in vitro dissolution data were obtained from three runs:

| Time (min.) | Percent Steroid Released (CV %) |
|---|---|
| 5 | 19.5 (49.5) |
| 10 | 29.9 (32.8) |
| 30 | 50.0 (23.0) |
| 60 | 61.6 (19.5) |
| 120 | 74.2 (19.2) |

EXAMPLE 5

With additional microcrystalline cellulose—containing sugar coated tablets prepared in the same manner as above, following Method B in six runs, the following data were obtained:

| Time (min.) | Percent Steroid Released (CV %) |
|---|---|
| 5 | 2.3 (34.4) |
| 10 | 8.2 (27.0) |
| 30 | 17.9 (16.1) |
| 60 | 26.5 (13.6) |
| 120 | 32.7 (16.6) |

EXAMPLE 6

And, following method C, with the tablets containing microcrystalline cellulose in the sugar coating, in three runs, the following data were obtained:

| Time (min.) | Percent Steroid Released (CV %) |
|---|---|
| 30 | 2.8 (34.4) |
| 60 | 4.1 (24.8) |
| 90 | 5.1 (22.3) |
| 120 | 6.4 (22.3) |

-continued

| Time (min.) | Percent Steroid Released (CV %) |
|---|---|
| 210 | 11.0 (19.4) |
| 300 | 14.3 (11.0) |

From these data it is apparent that a small amount of microcrystalline cellulose in the sugar coating (in this case 0.5% by weight of the sugar coating solids) has markedly retard the release rate of hormonal steroid.

EXAMPLE 7

Sugar coated tablets were prepared in which the sugar coat contained 0.0%, 0.5% or 2% microcrystalline cellulose in combination with 3.0% polyvinyl pyrrolidone, 10.0% medroxyprogesterone acetate and sucrose. These tablets were fed to four beagle dogs under fasting conditions and the blood plasma levels of steroid were determined at 0, 0.5, 1, 1.5, 2, 3, 5, 8, 12, 16, and 24 hours. The resulting data were plotted, the area under the curve (AUC) calculated for a twenty four hour period and the time at which the maximum plasma concentration occurred was determined to be as follows:

| Microcrystalline Cellulose % | AUC(0–24 Hrs) ngxhr/mL | tmax (Hr) | Cmax (ng/mL) |
|---|---|---|---|
| 0.0 | 345 | 0.6 | 37.8 |
| 0.5 | 294 | 1.0 | 36.9 |
| 2.0 | 294 | 1.1 | 24.6 |

From these in vivo dog data, it is obvious that a marked change in bioavailability of a hormonal steroid occurs as the concentration of microcrystalline cellulose in the sugar coating increases from 0.0 to one containing 0.5 to 2.0% microcrystalline cellulose. Thus, the rate of release of hormonal steroid incorporated in a sugar coating may be controlled by incorporation of very small amounts of microcrystalline cellulose into sugar coating.

EXAMPLE 8

Sugar coated tablets were prepared in which the sugar coat contained 0.25%, 0.5% or 0.8% microcrystalline cellulose in combination with 0.5% polyvinyl pyrrolidone, 5.0% medroxyprogesterone acetate and sucrose. These tablets were subjected to an in vitro dissolution test employing the USP Disintegration Apparatus (USP XX, <201>, p958) (1980) with a 0.54% sodium lauryl sulfate dissolution medium at 37° C. The following test data were obtained:

| | Percentage Medroxyprogesterone Acetate Dissolved (CV %) | | |
|---|---|---|---|
| Time (Minutes) | 0.25% Microcrystalline Cellulose | 0.5% Microcrystalline Cellulose | 0.8% Microcrystalline Cellulose |
| 15 | 97.8 (5.2) | 72.6 (9.5) | 32.4 (15.2) |
| 30 | 98.8 (5.3) | 89.9 (6.3) | 62.8 (8.2) |
| 45 | 99.3 (5.2) | 95.2 (5.6) | 76.6 (6.9) |
| 60 | 99.1 (5.2) | 98.3 (5.7) | 84.8 (6.6) |
| 90 | 99.9 (5.3) | 100.9 (6.0) | 94.4 (6.9) |
| 120 | 100.3 (5.6) | 102.4 (5.3) | 98.0 (7.1) |

These dosage forms were also evaluated in a human bioavailability study. The dosage forms were administered in a cross-over design to twelve healthy female subjects. Blood samples were collected at 0.5, 1, 1.5, 2, 2.5, 3, 4.5, 6, 8, and 12 hours and the plasma assayed for medroxyprogesterone acetate. The following data were obtained:

| Microcrystalline Cellulose | AUC (0–12 h) | tmax (hr) | Cmax (ng/mL) |
|---|---|---|---|
| 0.25% | 26.0 ± 14.3* | 2.9 ± 1.3 | 4.24 ± 3.0 |
| 0.5% | 25.8 ± 10.5 | 3.2 ± 1.2 | 3.88 ± 1.87 |
| 0.8% | 13.2 ± 4.0 | 3.9 ± 1.6 | 1.99 ± 0.73 |

*Mean values ± 1 Standard Deviation

From the in vitro dissolution and in vivo human bioavailability data, it is clear that the drug release characteristics and bioavailability of the hormonal steroid, are controlled by the concentration of microcrystalline cellulose in the sugar coating.

EXAMPLE 9

A sugar coating containing 5 mg of medrogestone in a matrix of sucrose with 0.4% microcrystalline cellulose and 0.5% polyvinyl pyrrolidone was applied to a sealed and sugar-coated tablet core. The in vitro dissolution profile of this dosage form was compared to that of a rapidly-disintegrating compressed tablet containing 5 mg of medrogenstone using the dissolution test described in <711> of USP XX, p. 959 (1980) employing Apparatus 2 operating at 50 r.p.m., with 900 mL of 0.54% sodium lauryl sulfate at 37° C. The following data were obtained:

| | Mean Percentage Medrogestone Released (CV %) | |
|---|---|---|
| Time (Minutes) | Conventional Rapidly Disintegrating Tablet | Sugar Coated Tablet Containing Medrogestone in Sugar Coat |
| 15 | 95 (2.0) | 6 (11.2) |
| 30 | 95 (2.9) | 11 (6.9) |
| 45 | 97 (1.6) | 15 (6.4) |
| 60 | 97 (1.9) | 18 (6.6) |
| 120 | 98 (1.9) | 25 (6.2) |

The dramatic effect of reduced dissolution of medrogestone when the hormone is incorporated in a sugar coat containing 0.4% microcrystalline cellulose is clearly demonstrated.

One preferred embodiment of this invention is a compressed tablet in which the tablet core contains a unit dose of an estrogenic compound or a mixture thereof in an amount of from about 0.1 to about 5.0 milligrams, or more preferably from about 0.3 to about 2.5 milligrams, in combination with standard excipient compression aids and fillers. Most desirably, the conjugated estrogens found in the tablet core comprise the naturally occurring conjugated estrogen product known as Premarin®. Over a sugar coat on the compressed tablet is applied an additional sugar coat containing about 1 to about 50 milligrams, and preferably about 1.5 to about 30 milligrams, of medroxyprogesterone acetate, a color coat, and finally, a polish coat. In other applications, it is preferable to employ a non-medicated core with a sugar coating containing a steroid such as trimegestone and more preferably, a sugar coating containing a mixture of steroids such as trimegestone and a conjugated estrogen.

What is claimed is:

1. In a pharmaceutical tablet comprising an internal compressed core and an external sugar coating, wherein said compressed core optionally contains no pharmacologically-active agent or one or more non-steroidal, pharmacologically-active agents that are conventionally administered in conjunction with a hormonal steroid, the improvement which comprises the incorporation of a hormonal steroid and a hormonal steroid release rate controlling amount of micro-crystalline cellulose in said sugar coating.

2. In a pharmaceutical tablet comprising a non-medicated, compressed core and a sugar coating, the improvement comprising incorporating a hormonal steroid and a hormonal steroid release rate controlling amount of microcrystalline cellulose in said sugar coating.

3. A pharmaceutical tablet of claim 1, in which said sugar present in said coating composition is sucrose.

4. A pharmaceutical tablet of claim 1 in which said hormonal steroid present in said sugar coating is medroxyprogesterone acetate, levonorgestrel, gestodene, medrogestone, estradiol, estriol, ethinylestradiol, mestranol, estrone, dienestrol, hexestrol, diethylstilbestrol, progesterone, desogestrel, norgestimate, hydroxyprogesterone, norethindrone, norethindone acetate, norgestrel, megestrol acetate, methyltestosterone, ethylestrenol, methandienone, oxandrolone, trimegestone or dienogest.

5. A pharmaceutical tablet of claim 1 in which said sugar coating comprises sucrose, from about 0.1% to about 3% microcrystalline cellulose, by weight, polyvinylpyrrolidone in an amount of from 0 to about 5% by weight and a hormonal steroid in an amount of from about 0.1 to about 20% by weight.

6. A pharmaceutical tablet of claim 1 in which said sugar coat contains an estrogenic steroid and a progestogenic steroid.

* * * * *